United States Patent [19]

Larue et al.

[11] Patent Number: 4,575,387

[45] Date of Patent: Mar. 11, 1986

[54] PROCESS FOR SEPARATING A MULTI-COMPONENT GASEOUS MIXTURE

[75] Inventors: Joseph Larue, Vaucresson; Alexandre Rojey, Garches, both of France

[73] Assignee: Institut Francais du Petrole, Rueil-Malmaison, France

[21] Appl. No.: 604,680

[22] Filed: Apr. 27, 1984

[30] Foreign Application Priority Data

Apr. 29, 1983 [FR] France ................. 83 07306

[51] Int. Cl.$^4$ .................. F25J 3/00; B01D 53/14
[52] U.S. Cl. ........................... 62/17; 62/23; 62/28; 55/56; 55/85; 210/737; 210/774
[58] Field of Search ............... 62/11, 17, 20, 23, 34, 62/38, 39, 40, 36, 28; 55/36, 37, 48, 49, 45, 64, 56, 68, 73, 85, 89; 210/774, 712, 718, 737, 773

[56] References Cited

U.S. PATENT DOCUMENTS 2,715,948 8/1955 Lewis et al. ................. 62/20
3,001,373 9/1961 Eastman et al. ............. 62/17
3,255,573 6/1966 Cox ............................... 55/45
3,753,335 8/1973 Morris .......................... 55/29
4,252,548 2/1981 Markbreiter et al. ........ 62/17

FOREIGN PATENT DOCUMENTS 1168012 12/1958 France .
1252030 1/1959 France .

Primary Examiner—S. Leon Bashore
Assistant Examiner—Andrew J. Anderson
Attorney, Agent, or Firm—Millen & White

[57] ABSTRACT

Process for separating the components of a gaseous mixture, saving energy and operating by demixing wherein the mixture to be separated is contacted under extracting conditions with a solvent which is then cooled down to a demixing temperature to provide two liquid phases, one of which has an increased extract content and the other an increased solvent content. The extract is recovered and the solvent recycled. The process can be used for numerous applications in the field of gas treatment.

16 Claims, 3 Drawing Figures

PROCESS FOR SEPARATING A MULTI-COMPONENT GASEOUS MIXTURE

The invention relates to a new fractionation process saving energy, applied to gaseous mixtures having several components.

BACKGROUND OF THE INVENTION

The fractionation of a mixture of several gaseous components is usually performed either by direct treatment of the mixture in gaseous form, for example by using techniques of adsorption on a solid, absorption in a liquid or permeation through membranes, or by liquefaction, by cooling and/or compressing the whole or a part of the gaseous mixture, often followed with the treatment of the resultant liquid by distillation or solvent extraction.

Any separation process consumes power; consequently, the power consumption of a fractionation process is an essential feature in the selection of such a process. In processes directly treating the mixture in gaseous form, i.e. by adsorption on a solid, absorption in a liquid or permeation in gaseous phase, the power consumption is relatively moderate but the separated fluid is a gas generally obtained at a relatively low pressure, which, depending on its subsequent use, may need to be recompressed and/or liquefied, thus requiring a high power consumption. In the case of a separation by distillation or extraction, the liquefaction takes place before the separation; it is often necessary, depending on the pressure in the rectification column, to cool the condenser of the distillation column down to a low temperature, which requires a further power consumption; it is notable, on the other hand, that the extraction by solvent is almost always followed with a distillation, for recycling the solvent. This second type of separation process, treating a liquid phase, provides a separated fluid in liquid phase but at the cost of a high power consumption.

In the past several years, numerous surveys have been conducted on the extraction by means of supercritical fluids. This technique takes advantage of the large selectivity variation of a fluid in response to temperature near its critical point. These processes offer advantages resulting from the great diffusion power and the low density and viscosity of the supercritical solvent; their power consumption is relatively low but they have the disadvantage of requiring very high pressures (usually from 5 to 30 MPa).

When separating a gaseous mixture by absorption in a liquid, a portion of the mixture components is dissolved in said absorption liquid and hence can be considered as being in liquid state; it is then re-extracted by increasing the temperature and/or decreasing the pressure and restoring the gaseous phase. As a matter of fact, it is a general rule that the absorption of a gas in a liquid is increasingly more substantial as the temperature is lower and the pressure higher.

The invention is based on a concept different from the process that is mentioned above, specifically on the concept of demixing, in two separate liquid phases, of a solution of a gas in a liquid, this demixing occurring, in some cases, as a result of a temperature decrease.

OBJECT OF THE INVENTION

The object of the present invention consists of separating, at low power cost, at least one of the components of a multi-component gaseous mixture, by taking advantage of the variations in solubility of said components in a solvent, in response to the temperature. All along the process of the invention, the solvent is used in conditions substantially remote from its critical state; in particular the higher temperature of the solvent in the process is at least 30° C. lower than the critical temperature of said solvent.

The present process concerns the separation of gaseous mixtures of at least two components; at least one of said components having preferably a critical temperature lower than 50° C., so that the mixture remains in gaseous phase within a wide range of temperatures and pressures.

The gaseous mixture to be separated into two components may comprise, for example, one or several saturated or unsaturated hydrocarbons, such for example as methane, ethane, propane, butane, ethylene, propylene, butene, butadiene, acetylene, one or more halogenated hydrocarbons, such for example as trichlorofluoromethane, dichlorodifluoromethane, chlorotrifluoromethane, tetrafluoromethane, trifluorobromomethane, chlorodifluoromethane, trifluoromethane, dichlorotetrafluoroethane, chloropentafluoroethane, other gases such for example as carbon dioxide, carbon monoxide, nitrogen, argon, oxygen, hydrogen, helium, hydrogen sulfide, sulfur dioxide, sulfur trioxide, chlorine, fluorine, steam, nitrogen oxides.

The gaseous mixture to separate into components may be, for example, a mixture of carbon dioxide and methane or a mixture of carbon dioxide and nitrogen, or a mixture of methane and ethane, or a mixture of hydrogen and ethane, or a mixture of hydrocarbons of different saturation degrees, for example a saturated hydrocarbon and an unsaturated hydrocarbon or a saturated or mono-olefinic hydrocarbon (or a mixture thereof) and a diolefinic hydrocarbon, or a mixture of halogenated hydrocarbons such, for example, as chlorodifluoroethane and chloropentafluoroethane, or a mixture of a halogenated hydrocarbon with another gas such, for example, as tetrafluoromethane and methane.

SUMMARY OF THE INVENTION

The invention comprises the steps of:

(a) placing in an extraction zone, under extracting conditions, the gaseous mixture to be fractionated with a solvent selective with respect to one of the gaseous mixture components, so as to form a solution of said component(s) in the solvent, the extraction zone being at a temperature at least 30° C. lower than the critical temperature of said solvent;

(b) separating said solution from the unextracted fraction of the gaseous mixture;

(c) cooling the separated solution, in at least one heat exchange zone, down to a temperature at which said separated solution can form two liquid phases, one of which ($F1$) is enriched with solvent and the other (F2) is enriched with the component(s) extracted during step (a);

(d) separating the two liquid phases (F1) and (F2) from each other;

(e) recycling to step (a) the phase (F1), enriched with solvent, so as to redissolve a portion of the gaseous mixture to be separated;

(f) recovering phase (F2), enriched with the component(s) extracted during step (a), which constitutes one of the products of the process.

In a preferred embodiment of the process, the phase (F1), enriched with solvent and/or the phase (F2), enriched with the components(s) extracted during step (a) pass through the heat exchange zone of step (c) so as to provide, at least partly, the cooling required in step (c).

When one (or both) phase(s) separated in step (d) is (are) not considered as sufficiently pure, a further purification of the concerned phase(s) can be achieved, for example by distillation.

The process according to the invention is based on the observed property according to which, in a solution of a compound in a solvent, generally a polar solvent, and under temperature and pressure conditions substantially remote from the critical point of said solvent, particularly when the maximum temperature of the process is at least 30° C. lower than the critical temperature of said solvent, a temperature decrease generally results in a decrease in the solubility of said compound in the solvent and a separation into two liquid phases occurs, one of the phases having a higher solvent concentration and the other a relatively higher concentration of said compound. It is thus possible to separate the solvent from the compound which was dissolved therein.

BRIEF DESCRIPTION OF THE DRAWINGS

The invention will be described more in detail with reference to the accompanying drawings illustrating, by way of example, particular embodiments which must not be considered as limiting the scope of the invention.

In these drawings.

Figure 1:
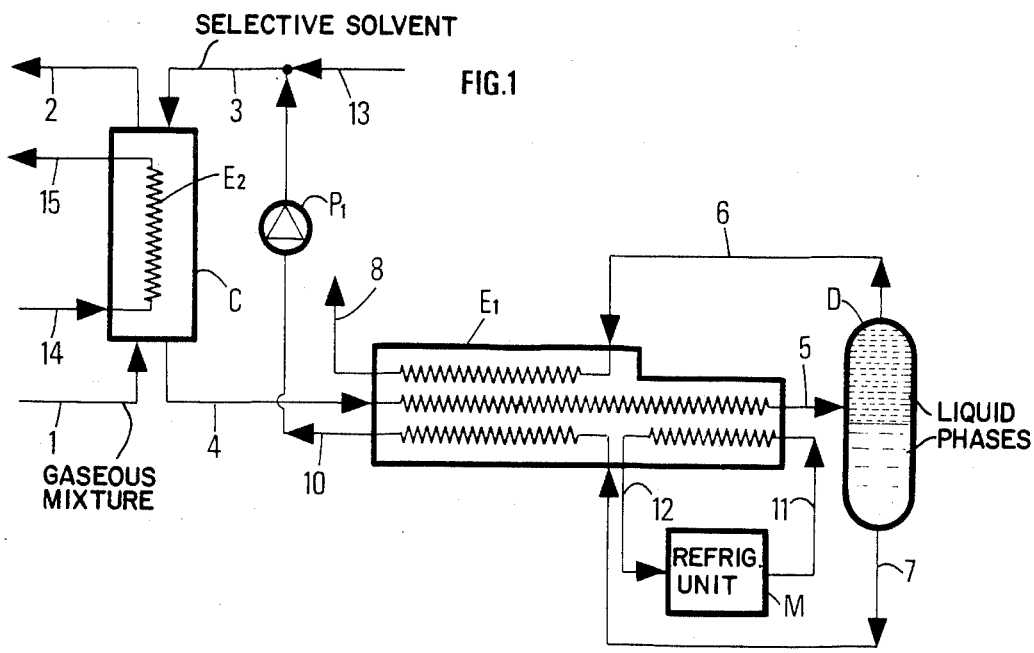
FIG. 1 is a flow-sheet illustrating a first embodiment of the process of the invention, which is of general use.

According to the flow-sheet of the FIG. 1, the gaseous mixture to be separated into components is supplied through line 1 to extractor C wherein it is contacted with a solvent (extraction liquid) supplied through line 3. In the temperature and pressure conditions prevailing in the extractor, one component or a portion of the components of the gaseous mixture is preferentially transferred to the solvent. This transfer may take place with thermal effect and, if so, it is possible to provide a heat exchange system $E_2$ in extractor C with an external heat carrier fed through line 14 and discharged through line 15. The temperature of extractor C is selected according to thermodynamic equilibrium criteria and is at least 30° C. lower than the critical temperature of the solvent. The portion of the gaseous mixture not dissolved in the solvent is discharged from the extractor C through line 2. The mixture of solvent with extracted product(s) is discharged from extractor C through line 4, fed to heat exchanger E1 wherein it is cooled down by heat exchange first with recycled products and then with a cold heat carrier supplied from the refrigerating unit M, which enters the exchanger E1 through line 11 and is discharged therefrom through line 12. The mixture is thus cooled down to such a temperature as to produce demixing in two liquid phases which are discharged from the heat exchanger E1 through line 5 and are separated in tank D. The phase of higher solvent content (supposed to be here the heavier phase) is discharged from tank D through line 7, penetrates in heat exchanger E1, wherein it is heated by heat exchange with the mixture supplied from line 4, is discharged from heat exchanger E1 through line 10 and passes through pump P1 to be recycled through line 3 to extractor C, in order to be used again for the extraction of the initial mixture to be separated. The other phase, enriched with extracted component(s) (supposed to be here the lighter phase), is discharged from tank D through line 6, penetrates into heat exchanger E1 wherein it is heated by heat exchange with the mixture supplied from line 4, is discharged from heat exchanger E1 through line 8 and is obtained, at the output from the process unit, in liquid state, in gaseous state or as a liquidvapor diphasic mixture, depending on its temperature and pressure level.

Additional solvent may be fed through line 13 in order to compensate for solvent losses due to the driving away of a portion thereof with the undissolved gaseous mixture discharged through line 2 and with the phase enriched with extract component(s) discharged through line 8.

In the settling tank D, the phase of high solvent content is often the heavy phase; however this is not a strict requirement, and when the phase of higher solvent content is the lighter phase, lines 6 and 7 are exchanged.

In lines 3,4,5,6,7,8 and 10, the pressure is substantially the same except for the pressure losses; pump P1 provides only for a low pressure difference corresponding to the pressure drops in the circuits and, consequently, the internal power consumption of the process is very low.

Figure 2:
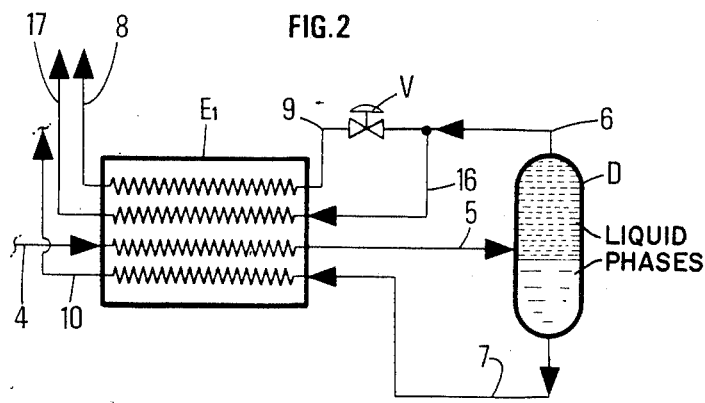
FIG. 2 illustrates a second embodiment avoiding the use of external cooling means.

The cooling of the mixture of solvent with the extracted component(s) discharged from extractor C through line 4 is performed in heat exchanger E1 by means of the obtained demixed products circulating through lines 6–8 and 7–10. The weight of the mixture circulating through line 4–5 is normally equal to the sum of the fluid weights circulating through lines 6–8 and 7–10. It is however necessary to subject the fluid circulating through line 4–5 to a further cooling by means of an additional refrigerating unit M, so as to generate, in heat exchanger E1, sufficient thermal differences between the fluids to cool the fluid circulating through line 4–5. When the heat losses through exchanger E1 are low, the heat amount taken by the fluid issued from the refrigerating unit and circulating through lines 11, 12 is low as compared to the total heat amount involved in heat exchanger E1; it is generally 10 to 30 times lower, thus resulting, for the process, in a low power consumption corresponding to power required by the refrigerating unit M to cool the fluid circulating through lines 11, 12 from its temperature in line 12 down to the temperature at which it is in line 11. It is possible to modify the flow-sheet of FIG. 1 so that the process no longer requires the use of a refrigerating unit and generates itself the cold required for its operation. The flow-sheet of this embodiment of the process is shown in FIG. 2. The gaseous mixture to be separated and the solvent are contacted in extractor C in a manner similar to that described with reference to FIG. 1. The mixture of solvent and extracted product(s) is discharged from extractor C through line 4 and enters exchanger E1 wherein it is cooled, by heat exchange with recycled products, down to a temperature such that demixing occurs in two liquid phases which are discharged from heat exchanger E1 through line 5 and are separated in tank D. The phase of higher solvent content (supposed to be here the heavier phase) is discharged from the tank through line 7, penetrates into the heat exchanger E1, wherein it is heated by heat exchange with the mixture supplied from line 4, thus at least partly coolling the same, is discharged from exchanger E1 through line 10 and passes through pump P1 for being recycled through line 3 to extractor C, similarly as in the embodiment corresponding to FIG. 1. The phase enriched with extracted component(s) (supposed to be here the lighter phase) is discharged from tank D through line 6 and separates in two portions. The larger fraction, generally from 60 to 95% of the amount circulating through line 6, passes through line 16, penetrates into the heat exchanger E1, wherein it is heated by heat exchange with the mixture circulating through line 4 - 5, thus providing a partial cooling thereof, flows out from heat exchanger E1 through line 17 and is discharged from the process unit. The smaller fraction, generally from 5 to 40% of the amount circulating through line 6, is expanded through valve V to such a pressure that its temperature at the output of valve V is at least 5° C. lower than the temperature in tank D, which is that of the fluid circulating through line 4 - 5 at the output of heat exchanger E1. It penetrates through line 9 into heat exchanger E1, wherein it vaporizes by heat exchange with the mixture circulating through line 4 - 5, thus providing for a partial cooling thereof, flows out from heat exchanger E1 through line 8 and is discharged from the process unit. In this embodiment the cold required for operation is produced by vaporization, in line 9 - 8, of a portion of the one or more extracted component(s), after demixing: here the power consumption of the process, which is that of the circulation pump P1, is negligible. As for the embodiment illustrated by FIG. 1, the solvent losses of the process may be compensated for by solvent addition through line 13.

Figure 3:
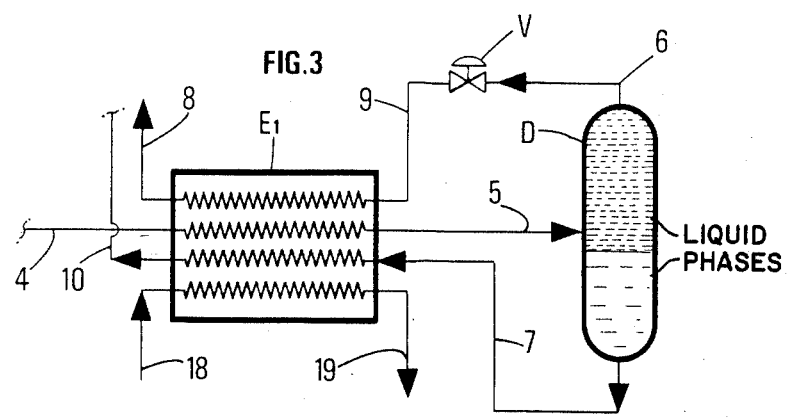
FIG. 3 illustrates a third embodiment wherein the process unit, in addition to its demixing effect, supplies cold to an external medium.

In a third embodiment, diagrammatically illustrated by FIG. 3, the process provides for the separation of the gaseous mixture, while simultaneously producing cooling. In that embodiment of the process, the cooling of the mixture of solvent with extracted component(s), the separation in two phases after demixing and the feed back of the phase of high solvent content to the extractor, are the same as in the above-described embodiment shown in FIG. 2. On the contrary in this third embodiment of FIG. 3, the phase enriched with extracted component(s) flows out from tank D through line 6, is completely expanded through valve V to such a pressure that the temperature at the output of valve V is at least 5° C. lower than the temperature in tank D, which is that of the fluid circulating through line 4 - 5 at the output of heat exchanger E1. It penetrates through line 9 into heat exchanger E1 wherein it vaporizes by heat exchange with the mixture circulating through line 4 - 5, thus providing for the partial cooling thereof, and with an external fluid supplied to exchanger E1 through line 18 and flowing out colder through line 19. It is discharged from exchanger E1 through line 8 and discharged from the process unit. In this embodiment the vaporization of the one or more extracted component(s) after demixing, in line 9 - 8, generates the cold required for lowering the temperature of the mixture circulating through line 4 - 5 and used for demixing and an additional cold amount which may be provided to an external fluid. As in the two above-described embodiments, the solvent losses in the process may be compensated for by addition of solvent through line 13.

In the three embodiments of the process diagrammatically shown in FIGS. 1, 2 and 3, the heat exchanger E1 is a 3- or 4-way exchanger: such heat exchangers are currently used in the cooling industry; they may consist for example of plate exchangers made of brazed aluminum or stainless steel or coiled exchangers. However, in the three embodiments of the process, the heat exchanger E1 may be replaced by several conventional two-way exchangers, which have the advantage of being more easily available.

The extraction step in extractor C is usually conducted at room temperature, but it may be advantagous, in some cases, to conduct the extraction at a temperature either higher or lower than room temperature, by making use of an additional heating or refrigerating source. The temperature in extractor C will always be at least 30° C. lower than the critical temperature of the solvent.

The pressure in the extraction zone will be preferably from 0.1 to 6 MPa absolute. This pressure remains unchanged all along the process, as far as pressure drops are not considered, except for the zones beyond the expansion valves in the second and third embodiments of the process, where the pressure is decreased to a value depending on the temperature desired for the considered fluid.

The temperature of the tank where the two liquid phases are separated after demixing, is obtained by means of a refrigerating unit M in the first embodiment of the process or by expansion of at least a portion of the demixed phase of high content of extracted component(s) in the two last embodiments of the process. The lower this temperature, the higher the respective concentrations in solvent and in extracted component(s) of the two demixed phases. This temperature is selected after having optimized the whole process and is preferably from 0° to −200° C.

The process according to the invention has the advantage, as compared to an extraction process by conventional solvent, of separating the one or more extracted component(s) or a large part thereof, from the solvent with a power consumption which may be low or non-existent, or even of producing cooling, depending on the process embodiment.

The gaseous mixtures to be separated must have, with respect to the solvent, the following properties:

(1) a substantial solubility in the solvent of at least one component of the gaseous mixture to be separated and selectivity of the solvent with respect to one component or to a portion of the components of the mixture.

(2) capacity of demixing at low temperature of the mixture of the solvent with the one or more extracted component(s) to form two separate liquid phases. This implies a sufficiently decreased temperature in exchanger E1 for causing the extracted component(s) to separate during the demixing in liquid and not in gaseous form.

The process of the invention differs from the extraction processes using supercritical fluids in that the solvent is never in conditions close to its critical state; in particular the temperature is always at least 30° C. lower than the critical temperature of the solvent.

The solvent is preferably a polar solvent such as water, an alcohol, a ketone, an aldehyde, an ether, a nitrogen derivative, a nitrile, an amide, ammonia, an amine, an ester, a sulfur compound or a halogenated compound. The chemical formulas of such solvents are, for example: $R-OH$, $R-CO-R'$, $R-CHO$, $R-O-R'$, $R-NO_2$, $R-CN$, $R'''-CONH_2$, $R''''-CONHR'$, $R'''-CONR'R''$, $R-NH_2$, $R-NH-R'$, $(RR'R'')N$, $RCOOR'$, wherein $R$, $R'$, $R''$, and $R'''$ are alkyl radicals containing 1 to 4 carbon atoms, R''' being optionally hydrogen. Cyclic compounds containing one of the above groups or other groups, for example lactone, lactame, sulfoxide, sulfone, may also be used. The solvent may also consist of a non-polar compound of hydrocarbon type having more than 4 carbon atoms, of aliphatic, naphthenic or aromatic type. The solvent may also be a halogenated hydrocarbon. Thus, the solvent may be for example methanol, ethanol, propanol, butanol, acetone, acetaldehyde, propionitrile, acetonitrile, nitropropane, nitroethane, nitromethane, ethyl ether, tetrahydrofuran, dimethylformamide, methylamine, dimethylamine, trimethylamine, perfluorooctane of formula $C_8H_{18}$, perfluoro butylperfluoro tetrahydrofuran of formula $C_8F_{16}O$, carbon sulfide, n-heptane, 2,2,4-trimethylpentane, toluene or a paraffinic, naphthenic, aromatic or synthetic oil. The solvent may be a pure product or a mixture of several solvents; it is possible in particular, by selecting the relative proportions of each solvent, to adjust the solving power to an optimum value for the considered case.

Examples of preferred associations, in the consecutive order of solvent-extracted gas-unextracted gas, are for example:
  acetone-ethane-hydrogen
  acetone-propane-nitrogen
  propanol and/or butanol and/or pentanol-carbon dioxide-methane
  propionitrile -ethane-methane
  pentane - sulfur dioxide - nitrogen The process according to the invention is illustrated by the following example.

EXAMPLE

In this example, the procedure conforms with the flowsheet of FIG. 2. The purpose of the operation is to recover a portion of the ethane contained in a hydrogen-ethane gaseous mixture. The hydrogen-ethane gaseous mixture to be separated is fed to extractor C through line 1. Its composition by mole is: hydrogen=0.42, ethane=0.58. Its pressure is 5 MPa its flow-rate by weight is 212 kg/h. In extractor C, which is a packed column, the gas mixture is contacted, at a temperature of about 20° C., with acetone, as solvent, supplied from line 3. In this extractor, ethane is partially dissolved in acetone, hydrogen remains in gaseous phase; the ethane amount dissolved in acetone is 101 kg/h. This dissolution is accompanied with a heat evolution; thus, for maintaining the temperature in extractor C at about 20° C., a heat exchanger E2 is incorporated to extractor C; water circulating therethrough is supplied through line 14 at 15° C. and discharged through line 15. Hydrogen of decreased ethane content is discharged from extractor C through line 2. Acetone, enriched with ethane, flows out from extractor C through line 4: its temperature is 20° C., its molar ethane content is 0.5, its flow rate by weight is 440 kg/h. The mixture is completely in liquid state; it is fed to exchanger E1 wherein it is cooled down by heat exchange to a temperature of −85° C. at which it is discharged from the exchanger through line 5. At this temperature a demixing occurs in two liquid phases which are separated by settling in tank D. The heavy phase, having a 75% molar acetone content, flows out from tank D through line 7 at a rate by weight of 333 kg/h, passes through heat exchanger E1 wherein it is heated by heat exchange, flows out therefrom through line 10 at a temperature of 15° C., passes through the circulation pump P1 and is recycled to extractor C through line 3. The light phase, whose molar ethane content is 97%, is discharged from tank D through line 6 and divides in two parts: one part flows through line 16 at a rate by weight of 89 kg/h, passes through exchanger E1 wherein it is heated by heat exchange, flows out therefrom through line 17, completely in liquid phase, at a temperature of 15° C. and under a pressure of 4.96 MPa. The other portion, at a rate by weight of 18 kg/h, is expanded through valve V to a pressure of 0.11 MPa and is supplied, through line 9, to heat exchanger E1, wherein it vaporizes by heat exchange and wherefrom it is discharged through line 8, completely vaporized, at a temperature of 15° C., under atmospheric pressure. Pure acetone is injected through line 13 at a rate of 8 kg/h in order to compensate for the acetone losses resulting from the driving along with hydrogen in extractor C and with ethane at the output of the process unit, through lines 8 and 17. The process resulted in a 50% recovery of the ethane content of the gas; 83% of which were obtained as liquid ethane under superatmospheric pressure and 17% as gaseous ethane under atmospheric pressure.

What is claimed as the invention is:

1. A process for fractionating a gaseous mixture comprising the steps of: (a) contacting in an extraction zone, under extracting conditions, the gaseous mixture to be fractionated with a solvent selective with respect to at least one of the components of the gaseous mixture, wherein the solvent has variable liquid solubility properties as a function of temperature and the solvent is employed in an amount sufficient to provide substantially only a single liquid solvent - extracted component(s) phase at one temperature and substantially only two liquid phases upon a reduction in temperature, said extraction zone being at a temperature at least 30° C. lower than the critical temperature of said solvent, (b) separating a solution being the single liquid solvent-extracted component(s) phase from residual gaseous mixture, (c) cooling the separated solution in at least one heat exchange zone, down to a temperature at which said solution forms two liquid phases, one of which (F1) is enriched with solvent and the other (F2) enriched with component(s) extracted in step (a), (d) separating the two liquid phases (F1 and F2) from each other, (e) recycling to step (a) the phase (F1) enriched with solvent so as to re-dissolve a portion of the gaseous mixture to be separated, and (f) recovering the phase (F2) enriched with component(s) extracted during step (a).

2. A process according to claim 1, wherein at least one of the components of the gaseous mixture to be separated has a critical temperature lower than 50° C.

3. A process according to claim 1, wherein said phase (F1), enriched with solvent, passes through the heat exchange zone of step(c) in order to take part in the temperature decrease required for step (c).

4. A process according to claim 1, wherein said phase (F2) enriched with components(s) extracted in step (a) passes through the heat exchange zone of step (c) so as to take part in the temperature decrease required for step (c).

5. A process according to claim 1, wherein an external cold fluid circulates through the heat exchange zone of step (c), so as to provide a part of the cooling required for step (c).

6. A process according to claim 1, wherein a part of said phase (F2) enriched with component(s) extracted in step(a) is expanded and passes through the heat exchange zone of step (c) while vaporizing to provide a part of the temperature decrease required for step(c).

7. A process according to claim 1, wherein the entirety of said phase (F2) enriched with component(s) extracted in step (a) is expanded and passes through the heat exchange zone of step (c) while vaporizing to provide, on the one hand, a part of the temperature decrease required for step (c) and, on the other hand, a temperature decrease of an external fluid circulating through said heat exchange zone.

8. A process according to claim 1, wherein the temperature at which the two liquid phases separate in step (d) is from 0° C. to −200° C.

9. A process according to claim 1, wherein the pressure in steps (a), (b), (c), (d), and (e) is from 0.1 to 6 MPa.

10. A process according to claim 1, wherein said gaseous mixture to be separated contains at least one of the following compounds: methane, ethane, propane, butane, ethylene, propylene, butene, butadiene, acetylene, trichlorofluoromethane, dichlorodifluoromethane, chlorotrifluoromethane, tetrafluoromethane, trifluorobromomethane, chlorodifluoromethane, trifluoromethane, dichlorotetrafluoroethane, chloropentafluoroethane, carbon dioxide, carbon monoxide, nitrogen, argon, oxygen, hydrogen, helium, hydrogen sulfide, sulfur dioxide, sulfur trioxide, chlorine, fluorine, nitrogen oxide, steam and wherein said solvent contains at least one of the following compounds: water, methanol, ethanol, propanol, butanol, acetone, acetaldehyde, propionitrile, acetonitrile, nitropropane, nitroethane nitromethane, ethylether, tetrahydrofuran, dimethylformamide, ammonia, methylamine, dimethylamine, trimethylamine, perfluorooctane, perfluorobutylperfluorotetrahydrofuran, pentane, hexane, heptane, octane, nonane, decane, benzene, toluene, xylene, α-methylnaphthalene, cyclopentane, cyclohexane, pentanol.

11. A process according to claim 1 wherein said gaseous mixture to be separated contains methane and carbon dioxide and wherein the solvent comprises one or more aliphatic alcohols containing from 3 to 5 carbon atoms.

12. A process according to claim 1, wherein said gaseous mixture to be separated contains ethane and hydrogen and wherein the solvent consists essentially of acetone.

13. A process according to claim 1, wherein said gaseous mixture to be separated contains propane and nitrogen and wherein the solvent consists essentially of acetone.

14. A process according to claim 1, wherein said gaseous mixture to be separated contains ethane and methane and wherein the solvent consists essentially of propionitrile.

15. A process according to claim 1, wherein said gaseous mixture to be separated contains sulfur dioxide and nitrogen and wherein the solvent consists essentially of pentane.

16. A process according to claim 1, wherein said gaseous mixture to be separated contains carbon dioxide and methane and wherein the solvent consists essentially of propanol, butanol or pentanol.

* * * * *